(12) United States Patent
Prokop

(10) Patent No.: US 6,726,934 B1
(45) Date of Patent: Apr. 27, 2004

(54) MICRO-PARTICULATE AND NANO-PARTICULATE POLYMERIC DELIVERY SYSTEM

(75) Inventor: Ales Prokop, Nashville, TN (US)

(73) Assignee: Vanderbilt University, Nashville, TN (US)

(*) Notice: Subject to any disclaimer, the term of this patent is extended or adjusted under 35 U.S.C. 154(b) by 588 days.

(21) Appl. No.: 09/169,459

(22) Filed: Oct. 9, 1998

Related U.S. Application Data

(60) Provisional application No. 60/062,943, filed on Oct. 9, 1997.

(51) Int. Cl.[7] .................. A61K 9/133; A61K 9/27; A61K 9/107
(52) U.S. Cl. ................. 424/500; 424/485; 424/496; 424/484; 424/488; 424/451; 424/450; 435/178
(58) Field of Search ................. 424/500, 489, 424/496, 484, 485, 488, 451, 450; 435/178

(56) References Cited

U.S. PATENT DOCUMENTS

| 4,933,185 | A | | 6/1990 | Wheatley | 424/461 |
| 5,462,866 | A | * | 10/1995 | Wang | 435/174 |
| 5,498,421 | A | * | 3/1996 | Grinstaff et al. | 424/450 |
| 5,529,777 | A | | 6/1996 | Andrianov et al. | 424/184.1 |
| 5,654,006 | A | * | 8/1997 | Fernandez et al. | 424/489 |
| 5,665,383 | A | * | 9/1997 | Grinstaff et al. | 424/450 |
| 5,700,459 | A | * | 12/1997 | Krone et al. | 424/78.08 |
| 5,997,900 | A | * | 12/1999 | Wang et al. | 424/451 |

* cited by examiner

Primary Examiner—Russell Travers
Assistant Examiner—Shahnam Sharareh
(74) Attorney, Agent, or Firm—Benjamin Aaron Adler

(57) ABSTRACT

The present invention provides a method of making particles useful in drug delivery, comprising the steps of: contacting polyanionic polymers with cations in a stirred reactor so that polyanions and the cations react to form particles.

12 Claims, 6 Drawing Sheets

MICRO-PARTICULATE AND NANO-PARTICULATE POLYMERIC DELIVERY SYSTEM

CROSS-REFERENCE TO RELATED APPLICATIONS

This application claims benefit of priority of application U.S. Ser. No. 60/062,943, filed Oct. 9, 1997, now abandoned.

BACKGROUND OF THE INVENTION

1. Field of the Invention

The present invention relates generally to the fields of pharmaceutical sciences, protein chemistry, polymer chemistry, colloid chemistry, immunology, and biomedical engineering. More specifically, the present invention relates to a novel microparticulate and nanoparticulate system for drug and antigen delivery, for gene (plasmid DNA) delivery and antisense RNA and DNA oligonucleotide delivery.

2. Description of the Related Art

Microparticulate systems are solid particles having a diameter of 1–2,000 $\mu$m (2 mm) and more preferably 1–10 $\mu$m (microparticles). Nanoparticulate system are submicroscopic colloidal particles (nanoparticles) having a diameter of preferably 50–500 nm (1,000 nm=1 $\mu$m). Both microparticles and nanoparticles can be formed from variety of materials, including synthetic polymers and biopolymers (proteins and polysaccharides). Both microparticles and nanoparticles are used as carriers for drugs and other biotechnology products, such as antigens, genes and antisense oligonucleotides.

In the controlled drug and antigen delivery area, microparticles and nanoparticles are formed in a mixture with molecules to be encapsulated within the particles, for subsequent sustained release. A number of different techniques are routinely used to make these particles from synthetic or natural polymers, including phase separation, precipitation, solvent evaporation, emulsification, and spray drying, or a combination of thereof [Desay, P.B., Microencapsulation of drugs by pan and air suspension technique. *Crit. Rev. Therapeut. Drug Carrier Syst.*, 5: 99–139 (1988); Berthold, A., Cremer, K., Kreuter, J. Preparation and characterization of chitosan microspheres as drug carrier for prednisolone sodium phosphate as model anti-inflammatory drugs. *J. Controlled Release* 39: 17–25 (1996); Watts, P. J., Davies, H. C., Melia, C. D. Microencapsulation using emulsification/solvent evaporation: An overview of techniques and applications. *Crit. Rev. Therapeut. Drug Carrier Syst.* 7: 235–159 (1990); Cowsar, D. R., Tice, T. R., Gilley, R. M., English, J. P. Poly(lactide-co-glycolide) microcapsules for controlled release of steroids. *Methods Enzymol.* 112: 101–116 (1985); Genta, I., 5 Pavanetto, F., Conti, B., Ginnoledi, P., Conte, U. Spray-drying for the preparation of chitosan microspheres. *Proc. Int. Symp. Controlled Release Mater.* 21: 616–617 (1994)].

Microparticles and nanoparticles can be prepared either from preformed polymers, such as polylactic acid, polylactic-glycolic acid [Cohen, et al., Controlled delivery systems for proteins based on poly(lactic/glycolic acid) microspheres. *Pharm. Res.* 8: 713–720 (1991)], or from a monomer during its polymerization, as is the case of polyalkylcyanoacrylates [Al-Khouri-Fallouh, et al., Development of new process for the manufacture of polyisobutyl-cyanoacrylate nanoparticles. *Int. J. Pharm.* 28: 125–132 (1986)]. Both of the above technologies have limited application because of the use of organic solvents during their preparation which leave residual organic solvents in the final product. Although the polyalkylcyanoacrylate nanoparticulate technology is also available as a water-based [Couvreur, et al., Biodegradable submicroscopic particles containing a biologically active substance and compositions containing them, U.S. Pat. No. 4,329,332 (1982)], animal studies demonstrated a presence of toxic degradation products [Cruz, et al., Interaction between polyalkylcyanoacrylate nanoparticles and peritoneal macrophages: MTT metabolism, NBT reduction, and NO production. *Pharm. Res.* 14: 73–79 (1997)].

Cell encapsulation [Chang, T. M. Hybrid artificial cells: Microencapsulation of living cells. *ASAIO Journal* 38: 128–130 (1992)] is a related technology which has been also explored for the purpose of making microparticles and nanoparticles. Such particles can be formed either by polymer precipitation, following the addition of a non-solvent or by gelling, following the addition of a small inorganic ion (salt) and of a complexing polymer (of an opposite charge). If enough time is allowed, the particle interior (core) can be completely gelled. Usually, the inner core material is typically of a polyanionic nature (negatively charged polymer), the particle membrane (corona) is made from a combination of polycation (positively charged polymer) and polyanion. The core material is usually atomized (nebulized) into small droplets and collected in a receiving bath containing a polycationic polymer solution. The reverse situation is also possible in which case the core material is polycationic and the receiving bath is polyanionic.

Several binary polymeric encapsulation systems have been described. An undesirable side effect of these encapsulation systems is that the membrane parameters are tied by a single chemical complex resulting from the ionic interactions. The inability to adjust particle parameters independently has limited the success of this system.

To overcome these limitations, a new multicomponent polymeric particle was designed which allows for independent modification of mechanical strength and permeability. Over one thousand combinations of polyanions and polycations were examined as polymer candidates suitable for encapsulation of living cells. Thirty-three combinations were found to be usable. However, the composition and concentrations do not allow for generating of small microparticles and nanoparticles, suitable for drug and antigen delivery.

The prior art is deficient in the lack of effective means of drug and antigen delivery, as well as plasmid and oligonucleotide delivery. The present invention fulfills this longstanding need and desire in the art.

SUMMARY OF THE INVENTION

To overcome the limitations of the prior art, the present invention provides new combinations of multicomponent water-soluble polymers which allow for modification of the particle size down to a desirable size, adequate mechanical strength, and desirable permeability and surface characteristics.

In one aspect, the present invention provides a method of preparing of microparticles and nanoparticles by means of a hollow ultrasonic device and a combination of polymers at relatively low concentrations. In another aspect, the present invention provides a method of production of micro- and nanoparticles in a single step process. In another aspect, the present invention provides a composition of matter of micro- and nanoparticles whereas the multicomponent combination of polymers is composed of a structural (gelling) polymer and a polymer providing the mechanical strength (crosslinking) and permeability control. In another aspect, the present invention provides a composition of matter and method of incorporation of antigens as an integral part of the particulate matter. In another aspect, the present invention provides a composition of matter and method of electrostatic and steric stabilization of particles whereas the stabilizing polymers are integral part of the particulate matter. Also provided is a method of direct use of particles generated in the single step as a vaccine delivered orally, nasally, rectally or vaginally, through inhalation to the lung, and by injection into muscle or skin or underneath the skin.

In another aspect, the present invention provides a composition of matter and method of production whereas the particles comprise of anionic DNA or oligonucleotide incorporated as an integral part of the matter. Further provided is a method of post-production processing of particles, composed of recovery and washing steps.

In another embodiment, the present invention provides a method of stabilization and composition of matter of particles by means of physiological crosslinking agents. Also provided is a method of cryoprotection and stabilization by means of lyophilization. In addition, the present invention provides methods of adjustment of biodegradation and composition of matter of particles by means of incorporation of suitable enzymes degrading polysaccharides, a method of immunization by means of oral, nasal, rectal or vaginal delivery of particles, by inhalation to the lung, and injection into muscle or skin or underneath the skin, a method of introduction of alum adjuvant as an integral part of particles and composition of matter, method of incorporation of mucoadhesive polymers into the particles and composition of matter.

In one aspect, the present invention provides a method of making particles useful in, for example, drug delivery, is provided, comprising the steps of: providing a stream of uniformly-sized submicron or few micron drops of polyanionic polymer solution by means of a hollow ultrasonic device; collecting said droplets in a stirred reactor provided with a cationic solution; wherein the polyanionic droplets and said cationic solution react to form particles. The particles have a polyanionic core and polyanionic/polycationic complex shell (corona) with excess of the positive charge on the particle periphery. Conversely, a stream of cationic solution of the size is collected in a polyanionic solution. The particles have polycationic core and polycationic/polyanionic complex shell (corona) with the excess of negative charge on the particle periphery. Alternatively, the polyanionic and polycationic solutions are mixed together in the ratio of 1:1 to 1:4 (the same ratio of polycationic to polyanionic solutions in the converse mode) and gently stirred for 5–10 minutes. For many combinations of polymers, a spontaneous formation of particles is observed. Still alternatively, streams of uniformly sized submicron droplets of both polyanionic and polycationic solutions are reacted in a gas-phase reactor.

Yet in another aspect of the present invention, there is provided a composition of matter comprising new multi-component systems to generate microparticles, composed of a structural (gelling) polymer and a polymer providing the mechanical strength and permeability control.

In addition, an embodiment may be where the individual components of the core polyanionic solution of polymers include concentrations of 0.01 wt-% to 0.5 wt-%. A more preferred embodiment would include a composition, where each component of the polyanions is at a concentration of 0.05 wt-% to 0.2 wt-%. In addition, the individual components of the corona cationic solution are at a concentration of 0.01 wt-% to 0.5 wt-%. In a most preferred embodiment, the polycations are at 0.05 wt-% to 0.2 wt-% and calcium chloride at 0.05 wt-% to 0.2 wt-% (and potassium chloride at 0.05 wt-% to 0.2 wt-% in case carrageenans are used as anionic polymers).

In another aspect of the present invention, there is provided a composition of matter comprising of the core polymers and cationic antigens, the latter being incorporated as an integral part of the ionically formed complex.

In addition, an embodiment may be where the individual components of the core cationic solution of polymers and inorganic salts include concentrations of 0.01 wt-% to 0.5 wt-%. A more preferred embodiment would include a composition, where each component of the polycations and of inorganic salts is at a concentration of 0.05 wt-% to 0.2 wt-%. In addition, the individual components of the corona polyanionic solution are at a concentration of 0.01 wt-% to 0.5 wt-%. In a most preferred embodiment, the polycations are at 0.05 wt-% to 0.2 wt-%.

In an additional aspect, the present invention may include the composition of matter comprising of charged polymeric surface modifiers (electrostatic stabilizers), the latter being incorporated in one step together with other polymeric components as an integral part of the complex. Similarly, a nonionic polymeric surface modifier (steric stabilizer) is integrated into the polymer structure via an entrapment. Both classes of surface modifiers are included to prevent particle aggregation upon their further processing.

In yet another aspect of the present invention, there is provided a method of direct use of the said reactor content in the case of oral, nasal, rectal, and vaginal application (vaccine), application by inhalation to the lung, and injection into muscle or skin or underneath the skin.

Another aspect of the present invention provides a composition of matter comprising of anionic polymers and anionic antigens (and plasmid DNA and antisense RNA and DNA oligonucleotide), the latter being incorporated as an integral part of the ionically formed complex.

In addition, the present invention includes a method of processing of said reactor content comprising the steps of: sedimenting or centrifuging said reactor mixture; collecting microparticles or nanoparticles as a pellet; rinsing said particles in a large excess of water, buffer, cryopreservation solution, electrostatic or steric stabilizer solution; separating said suspension by said sedimentation or centrifugation step; repeating said rinsing and separation steps; and reducing volume of the said suspension to about $\frac{1}{100}$th of the initial volume.

In an additional aspect of the present invention, there is provided a method of a chemical stabilization of the washed and isolated particles comprising the steps of: reacting the particles with a crosslinking agent; rinsing said particles in a large excess of water, buffer or a cryopreservation solution, electrostatic or steric stabilizer solution; separating the particles via sedimentation or centrifugation; repeating the rinsing and separation steps; and reducing volume of the suspension.

In a most preferred embodiment, the crosslinking agent is dextran polyaldehyde, a solution of photocrosslinking polymer, or a γ-glutamyl transferase enzyme. The reaction conditions are selected accordingly, but within the physiological realm.

In addition, the present invention may include a method of cryoprotecting said washed particles comprising the steps of: suspending the particles in a cryoprotective solution; and lyophilization of the suspension in a suitable lyophilization apparatus. A preferred embodiment would include glycerol, sucrose, PEG, PPG, PVP, block polymers of polyoxyethylene and polyoxypropylene, water soluble derivatized celluloses and some other agents at a concentration of 1 wt-% to 10 wt-%.

In another aspect of the present invention, there is provided a method of adjustment of biodegradability of polymeric mixtures, comprising the steps of: adding a suitable amount of suitable enzyme to a polysaccharide to be degraded; breaking down a polysaccharide at physiological conditions in vivo to degradation products which can be further broken to nonharmful products in animal/human body.

A preferred embodiment would include alginate-lyase (alginase) and carrageenase for polymer matrices containing alginate or carrageenans, in quantities allowing for controlled biodegradation in the range of one week to several months.

In an additional aspect of the present invention, there is provided a method of immunization of animals by means of oral delivery, or other known routes of vaccine administration, of encapsulated antigen in the particles, wherein the particles are taken up by M-cells in Peyer's patches of the epithelial lining of the upper intestinal tract and a build-up of secretory and systemic antibodies in blood is determined.

In still another aspect of the present invention, there is provided a method of introducing an adjuvant to potentiate an immunogenic effect. The adjuvant is preferably aluminum salt enabling to gel certain polysaccharides. The preferred embodiment could include CMC, CS and HV alginate as droplet forming anionic polymers, either individually, or in a mixture, and aluminum sulfate (or any other water soluble aluminum salt), calcium chloride and a suitable polycationic polymers as a corona forming mixture.

In yet another aspect of the present invention, there is provided a method of adding mucoadhesive polymers to the corona-forming bath to provide for sticking properties in relation to mucosal areas in animal/human body.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
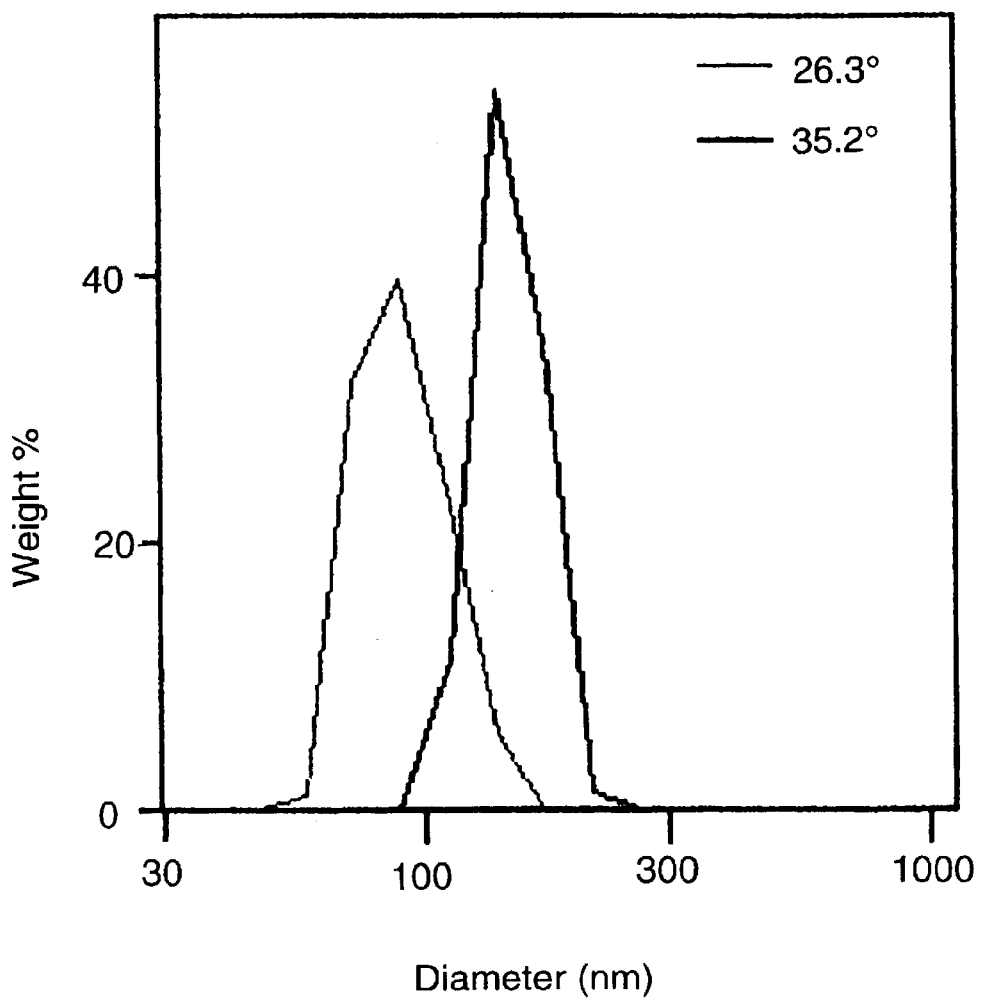
FIG. 1 shows the size distribution of nanoparticles with an integrated OVA immunogen.

As used herein, the term "reactor" shall refer to an enclosed vessel provided with or without a stirrer, allowing for a reaction to proceed in liquid or gas phases.

As used herein, the term "insoluble submicronic particles" shall refer to particles which remain solid in essentially water-based solutions, such as water, saline, PBS or a physiological buffer.

As used herein, the term "light scattering (Tyndall effect)" shall refer to light dispersion in many directions, resulting in a slightly milky suspension, visible by a human eye.

As used herein, the term "ultrasonic probe" shall refer to a hollow metallic tube whose tip oscillates many cycles per second as directed by a power imposed-upon it.

As used herein, the term "nanoparticle" shall refer to submicroscopic (less than 1 micrometer in size) solid object, essentially of regular or semi-regular shape.

As used herein, the term "corona" shall refer to an insoluble polymeric electrostatic complex composed of internal core polymer(s) and receiving bath polymer(s) molecularly bound in a close proximity.

As used herein, the term "structural (gelling) polymer" shall refer to polymers which can form semi-solid gelled structure by means of a small ion complexing.

As used herein, the term "core polymer" shall refer to a drop-forming polymer which represents an internal (central) part of the nanoparticle.

As used herein, the term "charged polymeric surface modifiers (electrostatic stabilizers)" shall refer to a polyelectrolyte (polymer) exhibiting a high charge density and as such providing the particle periphery with a high surface charge density, allowing for a strong repulsion force between adjoining particles.

As used herein, the term "nonionic polymeric surface modifier (steric stabilizer)" shall refer to nonionic (without charge) polymers with protruding side chains residing on the particle periphery and preventing intimate contact between adjoining particles.

As used herein, the term "cryoprotecting" shall refer to substances used for suspension of particles, which upon their water removal in vacuum allow particles to remain in individual and nonaggregating state In the description of the present invention, the following abbreviations may be used: SA-HV, high viscosity sodium alginate; CS, cellulose sulfate; k-carr, kappa carrageenan; LE-PE, low-esterified pectin (polygalacturonic acid); PGA, polyglutamic acid; CMC, carboxymethylcellulose; ChS-6, chondroitin sulfate-6; ChS-4, chondroitin sulfate-4; F-68, Pluronic copolymer; GGT, γ-glutamyl transferase; DPA, dextran polyaldehyde; PVSA, polyvinylsulphonic acid; PVPA, polyvinyl phosphonic acid; PAA, polyacrylic acid; PVA, polyvinylamine; OVA, ovalbumin, C-OVA, cationized ovalbumin; BSA, bovine serum albumin; AG, acacia gum; 3PP, pentasodium tripolyphosphate; PMCG, poly (methylene-co-guanidine) hydrochloride; SH, spermine hydrochloride; PS, protamine sulfate; PEI, polyethyleneimine; PEI-eth, polyethyleneimine-ethoxylated; PEI-EM, polyethyleneimine, epichlorhydrin modified; Q-PA, quartenized polyamide; pDADMAC-co-acrylamide, polydiallyldimethyl ammonium chloride-co-acrylamide; PBS, phosphate-buffered saline; PEG, polyethylene glycol; PPG, polypropylene glycol; polyethylene oxide (PEO); HEC, hydroxyethyl cellulose.

The present invention is directed to a composition of matter comprising various polyanion and polycation mixtures. A particularly usable combination is a combination of anionically charged antigen (or plasmid DNA or antisense oligonucleotide)/SA-HV/CS and SP/PMCG/CaCl$_2$.

It is specifically contemplated that pharmaceutical compositions may be prepared using a drug, or antigen, or plasmid DNA, or an antisense RNA oligonucleotide, encapsulated in the particles of the present invention. In such a case, the pharmaceutical composition may comprise a drug (or other biotechnology product) and a biologically acceptable matrix. A person having ordinary skill in this art would be able to determine readily, without undue experimentation, the appropriate concentrations of said biotechnology products, matrix composition and routes of administration of the particles of the present invention.

Additionally, the present invention provides methods for making particles, for their further surface modification, crosslinking and cryopreservation, and for an application of the encapsulated biotechnology products (drugs, plasmid DNA, antisense oligonucleotide), and for the immunization of an animal using encapsulated antigen.

The present invention is a water-based technology. Resulting particles consist of a dense polymeric core matrix, in which a drug (or antigen; plasmid DNA; antisense nucleotide) can be dispersed or dissolved, surrounded by a polymeric shell (corona). The particulate delivery systems have been widely used, but difficulties with biocompatibility, particle strength and the inability to define and modify parameters critical for such delivery vehicles has prevented this technology from achieving its full potential. A typical problem is a use of organic solvents for manufacturing particles, rather loose association of plasmid DNA within a liposome [Sternberg, et al., New structures in complex formation between DNA and cationic liposomes visualized by freeze-fracture electron microscopy. *FEBS Letters* 356: 361–366 (1994)] or a low stability of the DNA-spermine complex at physiological conditions [Milson, R. W., Bloomfield, V. A. Counterion-induced condensation of DNA. A light-scattering study. *Biochemistry* 18: 2192–2196 (1979)]. In addition, liposomes exhibit a very low incorporation of highly hydrophilic substances, such as DNA or polynucleotide.

Using a new combination of polymers and new encapsulation technology, generating very small particles, the present invention provides a multicomponent particle formed by polyelectrolyte complexation. In case the drug or targeted biological substance is polyelectrolyte by virtue of its nature, such components become an integral part of the particle. This new micro- and nanoparticulate technology has been applied as a vehicle for oral delivery of antigen, leading to subsequent immunization in vivo.

The following examples are given for the purpose of illustrating various embodiments of the invention and are not meant to limit the present invention in any fashion.

EXAMPLE 1

Particle Production Process

Particles may be made in a stirred reactor. In a more preferred mode, such a reactor is filled with a cationic solution. A mist of anionic droplets were generated by means of a hollow ultrasonic probe and introduced into the cationic solution residing in the reactor or receiving bath. Typically, 1–2 ml of anionic solution is extruded into 20 ml of cationic solution in a batch mode, resulting in a nonstoichiometric complex with an excess of cationic charge on the particle periphery. Instantly, insoluble submicronic particles are formed as evidenced by a light scattering (Tyndall effect). The reaction time can be adjusted. Typically, 1–2 hours is sufficient for particle maturation. This is due to their thermodynamic instability, large surface area and surface free energy. The size can be measured by means of a Malvern ZetaMaster (Malvern, UK).

The composition and combinations of anionic polymer mixture as well of the cationic receiving bath is essential to allow for adjustments in particle size, shape and uniformity. Conversely, droplets can be made from polycationic solution and the receiving bath contains then a polyanionic solution. Alternatively, the polyanionic and polycationic solutions are mixed together in the ratio of 1:1 to 1:4 (the same ratio of polycationic to polyanionic solutions in the converse mode) and gently stirred for 5–10 minutes (without the employment of the ultrasonic probe). For many combinations of polymers, a spontaneous formation of particles is observed.

Still alternatively, a continuous flow reactor system was constructed, composed of a continuous stream of submicron size drops of the core polyanionic solution; by means of a hollow ultrasonic device and a continuous stirred reactor filled with a corona cationic solution and provided with an inflow and outflow of this solution. The core solution is continuously introduced into the corona solution; the ratio of droplet (core)- to corona-forming solution flow rates is adjusted to result a nonstoichiometric polymeric complex. It is typically 1:20 to 3:20.

Still alternatively, two polymeric solutions (core an d corona) are allowed to react in a gas tubular reactor in form of mist, generated by two separate hollow ultrasonic devices. The product is easily separated because of large differences between the particle and air densities.

EXAMPLE 2

Particle Development: Polymer Screening

Many of thirty-three combinations of polymers, resulting from a multicomponent membrane encapsulation system, can be suitable for generation of small microparticles and nanoparticles. To develop new polymeric combinations of water-soluble polyanions and polycations, the instrumentation and process described in Example 1 was used. The criteria for selection was formation of submicroscopic particles (Tyndall effect). Individual polymers were tested for biocompatibility using an in vitro culture system with rat insulinoma cells (RIN 1046-38 cells, American Type Culture Collection, Rockville, Md.). Preferred combinations are listed in TABLE I. In contrast to cell microencapsulation systems requiring a combination of polymers resulting in a gelled interaction for sufficient membrane strength, small microparticulate and nanoparticulate systems result, in addition to the above, also from interactions resulting in a precipitated complex. Out of three different reaction products resulting from interactions of water-soluble polymerspolyelectrolytes of an opposite charge, soluble complex is the least desirable, not leading to particles. Precipitated complex is acceptable as long as it remains insoluble after its formation. The electrostatic insoluble complex is the best option. Both precipitated and electrostatic complexes are desirable for micro- and nanoparticle formation.

TABLE I

Multicomponent particulate systems

| Anionic components | Cationic components |
| --- | --- |
| SA-HV/3PP | Chit/calcium chloride |
| SA-HV/LE-pectin | BSA/calcium chloride |
| LE-pectin | PEI/calcium chloride |
| ChS-4/SA-HV | Gelatin A/calcium chloride |
| LE-pectin/SA-HV | Gelatin A/calcium chloride |
| Acacia/SA-HV | Gelatin A/calcium chloride |
| κ-carr/SA-HV | BSA/calcium chloride/potassium chloride |
| CS/SA-HV | Chit/calcium chloride |
| Sodium sulfate/SA-HV | Chit/calcium chloride |
| Gelatin B/SA-HV | Chit/calcium chloride |
| ChS-6/SA-HV | Chit/calcium chloride |
| ChS-4/SA-HV | Chit/calcium chloride |
| Gellan/SA-HV | PLL/calcium chloride |
| LE-pectin/SA-HV | Q-PA/calcium chloride |
| SA-HV/CS | Chit/calcium chloride |
| SA-HV/PGA | Chit/calcium chloride |
| CS/PGA | Chit/calcium chloride |
| Xanthan/gellan | PLL/calcium chloride |
| Xanthan/CS | PEI-eth/calcium chloride |
| Xanthan/κ-carr | PEI-eth/calcium chloride/potassium chloride |
| Xanthan/gellan | PEI-eth/calcium chloride |
| Xanthan/CS | PEI-EM/calcium chloride |
| Xanthan/CMC/ | pDADMAC-co-acrylamide/aluminum sulfate |
| CS/SA-HV | PVA/calcium chloride |
| CS/CMC | PVA/calcium chloride/aluminium sulfate |
| CS/gellan | PVA/calcium chloride |
| CMC/gellan | PVA/aluminium sulfate/calcium chloride |
| CS/CMC | Q-PA/calcium chloride |
| CS/xanthan | Q-PA/calcium chloride |
| CS/κ-carr | Q-PA/calcium chloride |
| CS/gellan | Q-PA/calcium chloride |
| CMC/xanthan | Q-PA/calcium chloride |
| CMC/κ-carr | Q-PA/calcium chloride |
| CMC/gellan | Q-PA/calcium chloride |
| Xanthan/κ-carr | Q-PA/calcium chloride |
| Xanthan/gellan | Q-PA/calcium chloride |
| CS/CMC | Polybrene |
| CS/xanthan | Polybrene |
| CS/κ-carr | Polybrene |
| CS/gellan | Polybrene |
| CMC/xanthan | Polybrene |
| CMC/κ-carr | Polybrene |
| CMC/gellan | Polybrene |
| Xanthan/κ-carr | Polybrene |
| Xanthan/gellan | Polybrene |
| PVPA/SA-HV | Chit/calcium chloride |
| PVSA/SA-HV | Chit/calcium chloride |
| PVPA/CS | Chit/calcium chloride |
| PVSA/CS | Chit/calcium chloride |
| SA-HV/3PP | PVA/calcium chloride |
| CS/3PP | PVA/calcium chloride |
| CMC/3PP | PVA/calcium chloride |
| CMC/3PP | PVA/calcium chloride/aluminum sulfate |
| Gellan/3PP | PVA/calcium chloride |
| Xanthan/SA-HV | PLL/SP |
| SA-HV/gellan | SH/PMCG |
| SA-HV/CS | SH/PMCG |
| SA-HV/gellan | PH/PMCG |
| SA-HV/CS | PH/PMCG |
| SA-HV/gellan | Polybrene/PMCG |
| SA-HV/CS | Polybrene/PMCG |
| κ-carr | PS/calcium chloride/potassium chloride |
| κ-carr/SA-HV | PS/calcium chloride/potassium chloride |
| κ-carr | SP/calcium chloride/potassium chloride |
| κ-carr/SA-HV | SP/calcium chloride/potassium chloride |
| κ-carr | Polybrene/calcium chloride/potassium chloride |
| κ-carr/SA-HV | Polybrene/calcium chloride/potassium chloride |
| κ-carr/heparin | PS/potassium chloride |
| κ-carr/heparin | Polybrene/potassium chloride |
| κ-carr/heparin | SH/potassium chloride |
| CS/heparin | PS/calcium chloride/potassium chloride |
| CS/heparin | Polybrene/calcium chloride/potassium chloride |
| CS/heparin | SH/calcium chloride/potassium chloride |
| PVSA/SA-HV | Chit/calcium chloride |
| κ-carr/gellan | PVA/calcium chloride |
| SA-HV/gellan | PVA/calcium chloride |
| PAA/SA-HV | Chit/calcium chloride |
| PAA/CS | Chit/calcium chloride |
| PAA/gellan | Chit/calcium chloride |
| PAA/κ-carr | Chit/calcium chloride |

EXAMPLE 3

Nanoparticle 1

This particle was generated using a droplet-forming polyanionic solution composed of 0.1 wt-% HV sodium alginate (SA-HV) and 0.05 wt-% chondroitin sulfate C (ChS-C) in water and corona-forming polycationic solution composed of 0.1 wt-% spermine hydrochloride (SH), 0.01 wt-% poly-L-lysine hydrochloride (PLL) and 0.2 wt-% calcium chloride in water. The chemicals used were: high viscosity sodium alginate (SA-HV) from Kelco/Merck (San Diego, Calif.) of average molecular weight $4.6 \times 10^5$; chondroitin sulfate-6 (ChS-6) from Sigma (St. Louis, Mo.); spermine hydrochloride (SH); poly-L-lysine (PLL), of average molecular weight $4.5 \times 10^4$; and calcium chloride. The ratio of droplet- to corona-forming reactants was 1.0:20. The particles were instantaneously formed in a batch system, allowed to react for 2 hours and their size and charge evaluated in the reaction mixture. The average size was 280 nm and the average charge 20.1 mV. Particles remained stable as individual entities during four week period at 4° C. The size of particles tended to increase upon their processing (washing in saline or water), if not stabilized.

EXAMPLE 4

Nanoparticle 2

This particle was generated using a droplet-forming polyanionic solution composed of 0.1wt-% HV sodium alginate (SA-HV) and 0.1 wt-% CS in water and corona-forming polycationic solution composed of 0.1 wt-% PMCG hydrochloride, and 0.2 wt-% calcium chloride in water. The polymers used were: cellulose sulfate, sodium salt (CS) from Janssen Chimica (Geel, Belgium) having a n average molecular weight $1.2 \times 10^6$; and poly(methylene-co-guanidine) hydrochloride (PMCG) from Scientific Polymer Products, Inc. (Ontario, N.Y.), with average molecular weight $5 \times 10^3$. The ratio of droplet- to corona-forming reactants was 1.5:20. The particles were instantaneously formed in a batch system, allowed to react for 1 hour and their size and charge evaluated in the reaction mixture. The size distribution was bimodal, with two categories: average size 3–5 μm and particles with average size <1 μm (Tyndall effect). The average charge 15.2 mV. Particles remained stable for 3 week observation period at 4° C. When these particles were further washed with saline or water, their size increased dramatically, unless stabilized.

EXAMPLE 5

Nanoparticles with Integrated Anionic Immunogen

These particles were generated using a droplet-forming polyanionic solution composed of 0.1 wt-% AG, 0.1 wt-%

OVA and 0.1 wt-% SA-HV in water, adjusted to pH 4.0 and corona-forming polycationic solution composed of 0.2 wt-% BSA, and 0.2 wt-% calcium chloride in water, also adjusted to pH 4.0. The OVA was used as a model anionic antigen. The ratio of droplet- to corona-forming reactants was 1:20. The polymers used were: acacia gum (AG) from Sigma, average molecular weight $4.5 \times 10^5$, isoelectric point (pI) 4.0; egg ovalbumin (OVA) from Sigma, average molecular weight $4.2 \times 10^4$, pI 4.6; and bovine serum albumin (BSA) from Sigma, with average molecular weight $6.7 \times 10^4$, pI 5.4. The particles were instantaneously formed, allowed to react for 1 hour and their size and charge evaluated in the reaction mixture. The average size was 430 nm and the average charge 15.5 mV. Particles remained stable for 4 week observation time at 4° C. When these particles were further washed with saline or water, they slowly dissolved over a period of few days, unless stabilized by crosslinking.

EXAMPLE 6

Nanoparticles with Integrated Cationic Immunogen

Figure 2:
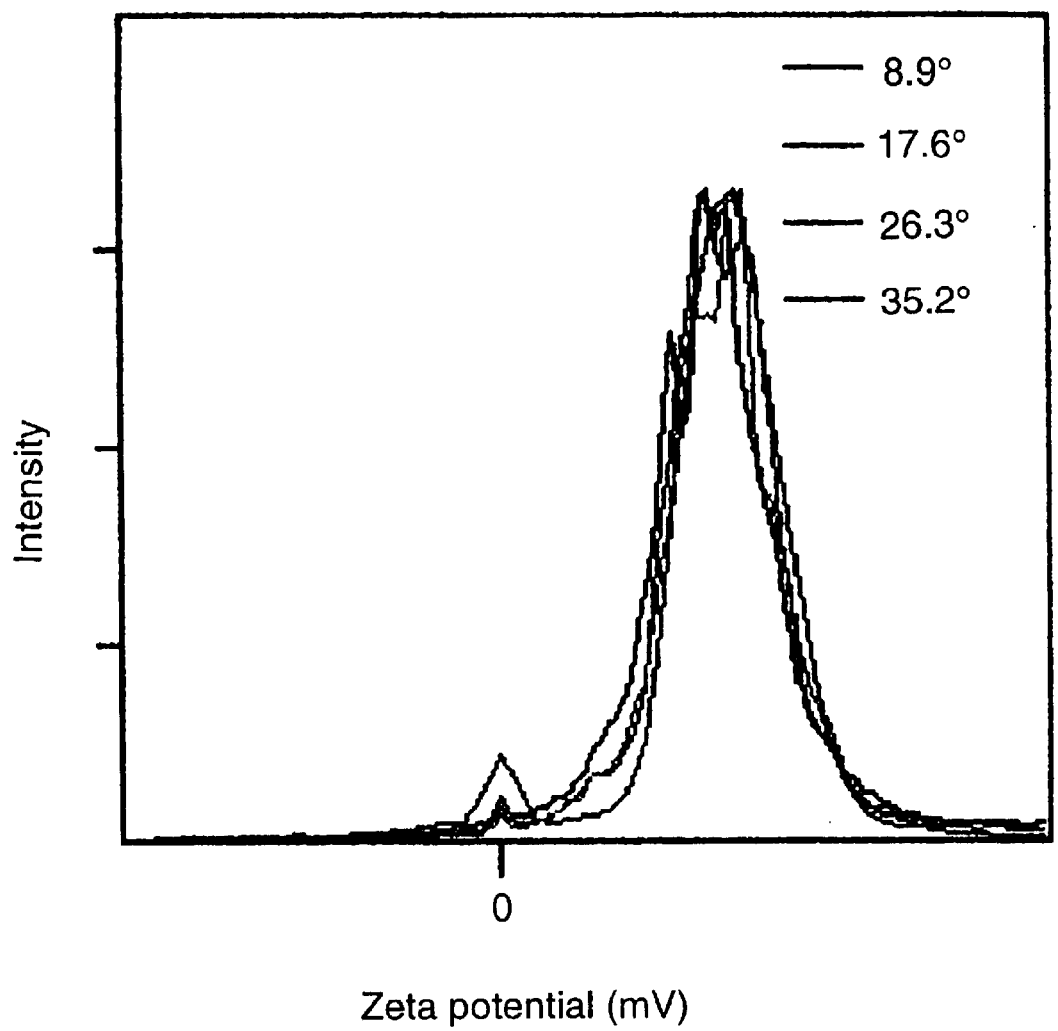
FIG. 2 shows the charge distribution of nanoparticles with an integrated OVA immunogen.

These particles were generated using a droplet-forming polycationic solution composed of 0.1 wt-% Chit, 0.1 wt-% C-OVA and 0.2 wt-% calcium chloride in water, and corona-forming polyanionic solution composed of 0.2 wt-% PGA, and 0.1 wt-% SA-HV in water. The C-OVA was used as a model cationic antigen. The ratio of droplet- to corona-forming reactants was 1:20. The polymers used were: chitosan glutamate Protasan HV (Chit) from Pronova Biopolymers (Drammen, Norway), average molecular weight $7.5 \times 10^5$; cationized ovalbumin (C-OVA), synthesized in-house according to published procedure [Altmann, K. G. Effect of cationization on anti-hapten antibody response in sheep and mice. *Immunol. Cell Biology* 71: 517–525 (1993)], average molecular weight $4.2 \times 10^4$, pI 10.4; and pentasodium tripolyphosphate (3PP) from Sigma. The particles were instantaneously formed, allowed to react for 1 hour and their size and charge evaluated in the reaction mixture. The average size was 220 nm (FIG. 1) and the average charge $-17.0$ mV (FIG. 2). Particles remained stable for 5 week observation time at 4° C.

EXAMPLE 7

Electrostatic Surface Stabilization of Nanoparticles

These particles were generated using a droplet-forming polyanionic solution composed of 0.1 wt-% SA-HV in water, and corona-forming polycationic solution composed of 0.05 wt-% PLL in water. The ratio of droplet- to corona-forming reactants was 1:20. The particles were instantaneously formed, allowed to react for 1 hour and their size and charge evaluated in the reaction mixture. The average size was 220 nm and the average charge 25.4 mV. When particles were washed in water or in saline, they aggregated and formed patches floating on the top of solution. When 0.05 wt-% BSA solution (pH 5.0) was used for successive washing and resuspending, the original size remained unchanged.

EXAMPLE 8

Steric Surface Stabilization of Nanoparticles

These particles were generated using a droplet-forming polyanionic solution identical to that used in Example 4, with an additional 0.1 wt-% F-68 added. The corona-forming polycationic solution was same as in Example 4. Pluronic F-68 (BASF, Mount Olive, N.J.) is a water soluble nonionic block polymer composed of polyoxyethylene and polyoxypropylene segments. In contrast to particles generated in Example 4, particle size remained unchanged during the washing steps. Similar results were obtained for other nonionic block co-polymers [Emanuele, R. M., Balasabramanian, M., Allandan, H. Polyoxypropylene/polyoxyethylene copolymers with improved biological activity, U.S. Pat. No. 5,567,859 (1996)(CytRx Corp.), Hunter, R. J. Methods and vaccines comprising surface-active copolymers, U.S. Pat. No. 5,534,372 (1996)].

EXAMPLE 9

Direct Use of the Reaction Product for Oral Antigen Delivery

These particles were generated using droplet-forming polymeric combination identical to that used in Example 4, except the polyanionic mixture had additional polymer, 0.1 wt-% OVA. The reaction mixture, after 2 hour maturation time, was applied as such, without washing, into experimental animals (male Sprague-Dawley adult rats (200–250 g wt., 12–15 weeks old, Harlow). About 1 mg of dry weight of nanoparticles in the reaction mixture has been administered orally into the stomach of each animal. The nonloaded (no OVA) nanoparticles were also administered to control animals, in addition to a soluble antigen (OVA). ELISA assay of secretory IgA and serum IgG antibodies was carried out as described [Challacombe, et al., Enhanced secretory IgA and systemic IgG antibody response after oral immunization with biodegradable microcapsules containing antigen. *Immunology* 76: 164–168 (1992)]. Primary and secondary immunization protocol was used, consisting of three successive days at week 0 and week 4. Immunizations with OVA-nanoparticles resulted in dramatically greater levels of both secretory and serum antibodies (about 30–50 times) than those found with the soluble antigen. In another set of experiments nonloaded nanoparticles (no OVA) were separately tested in simulated gastric (pH 2) and intestinal (pH 8.3) solutions for their stability. The nanoparticles remained stable during the observation period of one week. However, a separate experiment revealed that OVA-loaded nanoparticles released about 40% OVA in 2 hours at pH 2 and continued to release thereafter.

EXAMPLE 10

Particle Recovery

Particles were separated as in Examples 4 and 5. Average size was 390 nm and average charge 15.9 mV. After a 2 hour maturation time, particles were centrifuged at 15° C. for 15 minutes at 10,000 g in a refrigerated Beckman centrifuge L5-50 (Beckman Instruments, Fullerton, Calif.). Next, the supernatant was carefully aspirated off by means of pipette without disturbing the layer of particles at the bottom of 35 ml centrifuge tubes. The sediment was then resuspended in 1 ml water by repeated pipetting in and out, tubes filled up to 35 ml with water and centrifuged again. After removing the supernatant, a dense suspension of particles (1 ml) was evaluated for size and charge. The average size was 450 nm and average charge +10.2 mV (at pH 6.8).

EXAMPLE 11

Continuous Production of Nanoparticles

These particles were generated using a droplet-forming polyanionic solution containing 0.1 wt-% 3PP, 0.1 wt-% kappa-carrageenan and 0.3 wt-% OVA in water, and corona-forming solution composed of 0.05 wt-% chit, 0.1 wt-% CaCl$_2$ and 1 wt-% F-68 in water. The droplet-forming solution was continuously fed at flow rate 1, 1.5 and 2 ml/min into a continuous stirred tank reactor of 50 ml working volume maintained at flow rate of 20 ml/min by core-forming solution. The reactor was operated for 10–20 min to reach a steady-state. Samples of reaction mixture were directly analyzed for size and charge (Table II). Data on size and charge obtained between 10 and 20 min of continuous operation indicated that the product quality can be easily maintained, as judged by invariance in size and charge. Separately, large volumes of reaction mixture collected at each flow rate of droplet-forming solution were processed by centrifugation and washing. The size and charge between the direct and processed samples were not significant. The continuous production allows for independent adjustment in size and charge by varying the OVA and F-68 concentrations (data not shown).

TABLE II

Size and charge of continuously produced nanoparticles

| | Core polymer flow rate (ml/min) | | |
|---|---|---|---|
| | 1.0 | 1.5 | 2.0 |
| Size (nm) | 350 | 457 | 655 |
| Charge (mV) | 45.1 | 38.2 | 30.3 |

EXAMPLE 12

Crosslinking of Nanoparticles

These particles were generated using a droplet-forming polyanionic solution composed of 0.0125 wt-% HMP (Sigma), 0.025 wt-% gellan (Kelco), 0.025 wt-% SA-HV and 12 mg tetanus toxoid antigen (TT) (Connaught Labs., Swiftwater, Pa.) in water, and corona-forming polycationic solution composed of 0.075 wt-% PMCG, 0.05 wt-% CaCl$_2$ and 2 wt-% F-68 in water. The ratio of droplet- to corona-forming reactants was 3.5:20. Particles were prepared and processed as in Example 10. A portion of water-washed particles was resuspended in 0.01 wt-% dextran polyaldehyde solution (DPA, CarboMer, Westborough, Mass.), average molecular weight $4 \times 10^4$, and incubated in a bicarbonate buffer (pH 8.3) at 37° C. for 15 minutes. Another portion of washed particles was treated with 0.01 wt-% γ-glutamyl transferase (GGT, Sigma) in TRIZMA (Sigma) buffer (pH 8.5) with 10 mM calcium chloride at 20° C. for 30 minutes. Another portion was treated with 0.1 wt-% solution of polyvinyl alcohol bearing styrylpyridinium group (synthesized in-house) [Ichimura, K, Watanabe, S. Preparation and characterization of photo-crosslinkable poly(vinyl alcohol). *J. Polymer Science*, Polymer Chemistry Edition 20:1419–1432 (1982)] and exposed to a visible light source (halogen lamp with a cut-off UV filter). Following these crosslinking steps, particles were rinsed in a large excess of water, let sediment and resuspended in a small volume of water. Particles stabilized via such crosslinking remained stable for observed 3 weeks at 4° C., compared to 3–5 days without a such treatment.

In another set of experiments, particles were prepared a s above but the droplet-forming solution contained an additional polymer, PDA. The concentrations used were 0.00014 wt-%, 0.0007 wt-% and 0.0014 wt-%. Washed particles were resuspended in a bicarbonate buffer (pH 8.3), incubated for 15 min at 37° C. and subsequently washed again. The size and charge of crosslinked particles was not substantially different from those without the crosslinking. A portion of particles was incubated in a Tris buffer (pH 1.85) for 1.5 hour and released protein (TT) was assayed in the supernatant by means of the Pierce method (Table III). The average exposure time 1.5 hours represents, approximately, the residence time of particles in the stomachs of experimental animals.

TABLE III

TT release as affected by crosslinking

| Concentration of PDA | Protein release (% total) |
|---|---|
| 0 (no crosslinking) | 29.5 |
| 0.00014 wt - % | 11.8 |
| 0.0007 wt - % | 10.4 |
| 0.0014 wt - % | 7.6 |

EXAMPLE 13

Cryoprotection of Nanoparticles

Particles were prepared as in Example 5. First, they were separated by centrifugation at 10,000×g and then rinsed in water and resuspended in a solution containing a cryoprotective agent. A concentrated suspension of particles was then frozen in a mixture of ethanol-dry ice and lyophilized thereafter using a lyophilization apparatus (The Virtis Co., Gardiner, N.Y.), under a vacuum. In this case, only two cryoprotective agents were tested on two portions of particulate suspension: 2 wt-% PEG (Sigma, average molecular weight $8 \times 10^3$, and 2 wt-% HEC (Scientific Polymers Products). The resulting product was particulate and easily resuspendable in water. The average size of particles increased from the original 425 nm to 625 nm, or 450 nm to 590 nm, respectively.

EXAMPLE 14

Adjustment of Nanoparticle Biodegradation

Particles were prepared as in Example 1, except that the core polymeric mixture was adjusted to allow for a slow degradation when applied in vivo. A purified alginase-lyase (alginase) was obtained courtesy of N.L. Schiller [Schiller, et al., Characterization of the Pseudomonas aeruginosa alginate lyase gene (algL): Cloning, sequencing, and expression in *Escherichia coli*. *J. Bacteriology* 175: 4780–4789 (1993)] and used at levels of 1 and 10 µg/L in the core solution. Particles were prepared, washed in water and incubated 20 minutes at 37° C. in a solution consisting of: TRIS buffer (pH 8.5), 9 mM magnesium chloride, 0.5 M sodium chloride. As a criterion of biodegradation, a time to achieve a visible breakdown of particles was noted. Particles containing 1 µg/L disintegrated in 32 days, particles containing 10 µg/L in 4 days. The control particles (no enzyme) remained intact even after 6 weeks.

EXAMPLE 15

Use of Nanoparticles for Immunization of Animals

Figure 3:
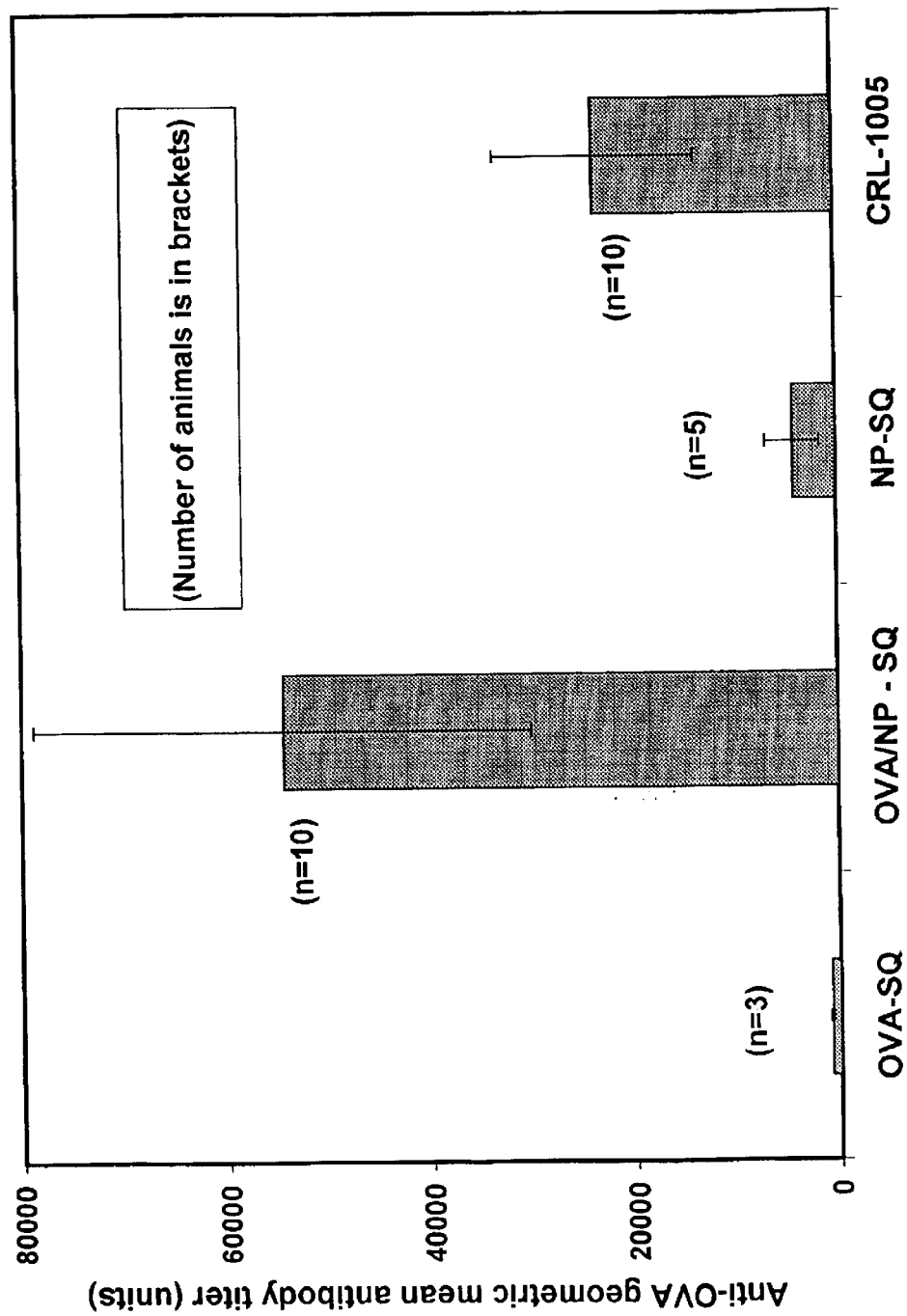
FIG. 3 depicts the response to subcutaneous nanoparticulate OVA antigen (second column) in terms of anti-OVA antibodies. The bars represent the average +/−SD.

Particles were prepared as in Example 11, stabilized by cross-linking with PDA, as specified in Example 12 (PDA concentration used was 0.001 wt-%), and applied subcutaneously in animals, as specified in Example 9. Results were similar to those reported in Example 9. Total serum anti- OVA antibody titers are presented in FIG. 3. In this figure, OVA-SQ represents the application of soluble antigen OVA, OVA/NP-SQ a subcutaneous application of nanoparticles loaded with OVA, NP-SQ a subcutaneous application of empty (no OVA) nanoparticles (negative control) and CRL-1005 (Vaxcel, Norcross, Ga.) was a positive control (OVA formulated with help of a polymeric adjuvant similar to those mentioned in Example 8). The values are presented in FIG. 3 as the average bar height (n=number of animals) +/−SD (standard deviation).

Figure 4:
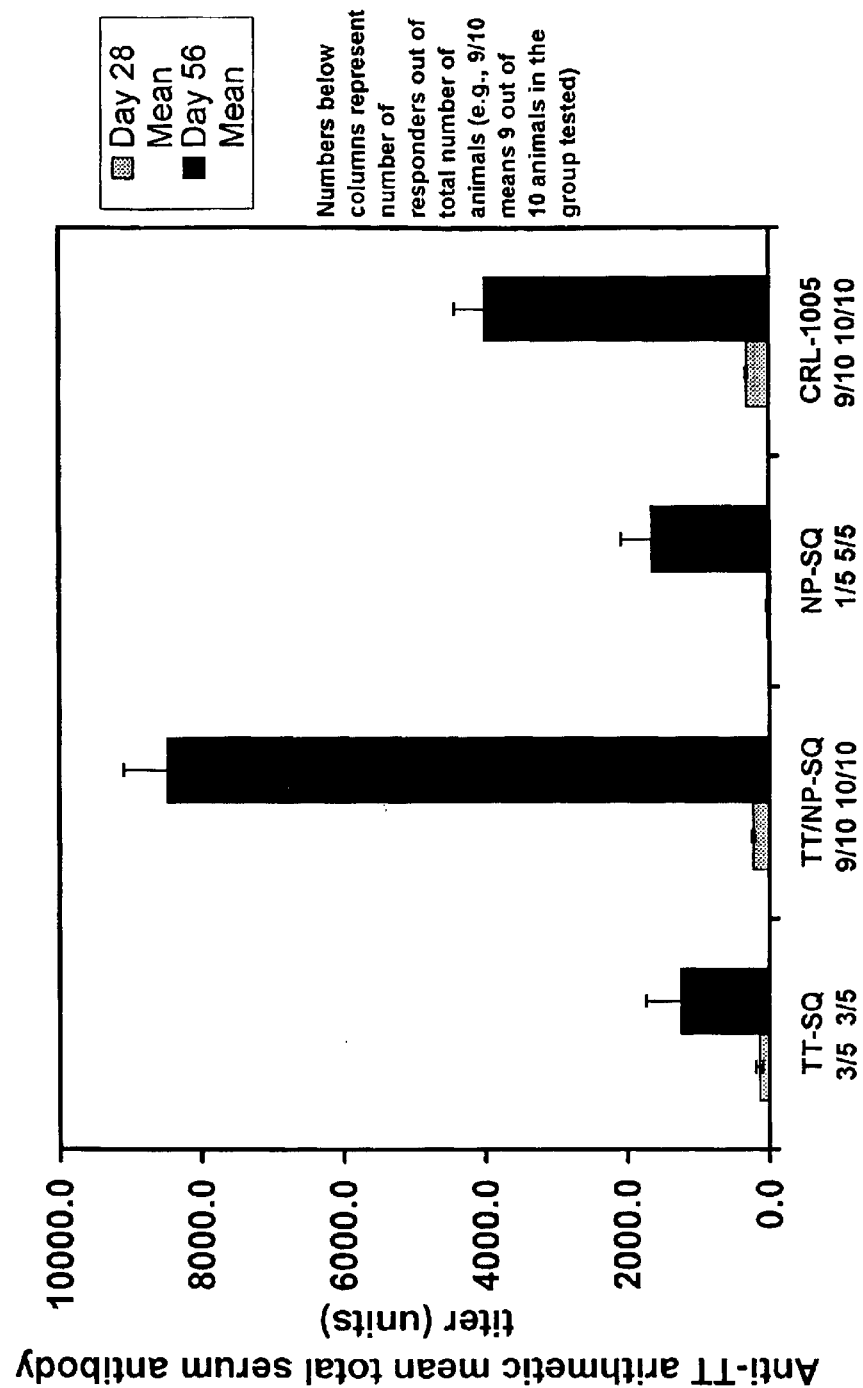
FIG. 4 depicts the response to subcutaneous nanoparticulate TT antigen (second column) in terms of anti-TT antibodies. The bars represent the average +/−SD.

For OVA-SQ, only 3 out of 10 animals per group responded (the others failed to respond at all). For OVA/NP-SQ, all 10 responded. For NP-SQ, 5 out of 10 responded, and for CRL-1005, all 10 responded. Clearly, the OVA entrapped in the nanoparticles is the most effective at eliciting a response. Similar results were obtained with the TT antigen, represented in tabular form in Table IV and graphically in FIG. 4.

TABLE IV

Response to subcutaneous nanoparticulate TT antigen

|  |  | TT-SQ | TT/NP-SQ | NP-SQ | CRL-1005 |
|---|---|---|---|---|---|
| Day 28 | Mean | 146.0 | 230.0 | 34.0 | 319.0 |
|  | SD | 53.0 | 22.0 | 13.0 | 22.0 |
| Day 56 | Mean | 1243.0 | 8467.0 | 1646.0 | 3998.0 |
|  | SD | 487.0 | 614.0 | 431.0 | 427.0 |

EXAMPLE 16

Use of Aluminum Adjuvant

Nanoparticles were generated using droplet-forming polyanionic mixture composed of 0.1 wt-% CMC and 0.05 wt-% CS in water and corona-forming polycationic mixture composed of 0.2 wt-% aluminum sulfate and 0.1 wt-% PMCG in water. Chemicals used were: aluminum sulfate (Sigma) and carboxymethylcellulose (brand 7MF, CMC, Aqualon/Hercules, Wilmington, Del.), having medium molecular weight. Aluminum sulfate was incorporated into the nanoparticles as it is known to potentiate antigenic response [Cox, J. C., Coulter, A. R., Adjuvants—a classification and review of their modes of action, *Vaccine* 15:248–256 (1997)]. Particles formed instantaneously and their average size was 225 nm and average charge 25.4 mV. They were very stable at washing and further processing (no aggregation).

EXAMPLE 17

Generation of Nanoparticles

These particles were generated using a droplet-forming polyanionic solution composed of 0.05 wt-% SA-HV, 0.05 wt-% CS and 0.008 wt-% pCEPluc plasmid in water, and corona-forming olycationic solution composed of 0.05 wt-% SH, 0.065 wt-% PMCG, 0.05 wt-% $CaCl_2$ and 1.0 wt-% F-68 in water. The latter solution was used as a plasmid condensing agent. pCEPluc is plasmid with a CEP promoter, covalently linked to a luciferase gene as a reporter gene. This plasmid was expressed in a bacterium, grown in a culture and isolated in-house. The ratio of droplet- to corona-forming reactants was 1:10. For particle generation, a special glass double-nozzle atomizer was used. The droplet-forming solution was applied in the internal nozzle, while the air was used to strip particles off the internal nozzle and atomize them into submicron-range size using a n internal nozzle. The droplets were then collected in the corona-forming solution. Such device was used because the DNA molecule is sensitive to sonication and can be substantially damaged. The particles were separated by centrifugation and washed. Their size and charge were 190 nm and +24.0 mV, respectively. These particles exhibited an expression of luciferase enzyme in several in vitro cell culture lines.

EXAMPLE 18

Nanoparticles Loaded with a Cationic Drug

While the preparation of particles with uncharged or anionically charged drugs can be prepared in a similar way as described in Example 5 (with replacement of OVA by such a drug), nanoparticles with integrated cationic drug are prepared by a reverse encapsulation, similar to Example 6. These particles are generated using a droplet-forming polycationic solution composed of 0.05 wt-% chit, 0.05 wt-% PVA (15k, Air Products and Chemicals, Allentown, Pa.), 0.05 wt-% CaCl2 and 0.1 wt-% gentamycin sulfate (Sigma) in water (adjusted to pH 5.0) and corona-forming polyanionic solution composed of 0.1 wt-% 3PP and 1 wt-% F-68 in water. The ratio of droplet- to corona-forming reactants was 1.5:20 or 2:20. The particles were instantaneously formed, allowed to react one hour and their size and charge evaluated after a standard separation and washing. The average size was 86 nm and the average charge was +34.4 mV.

EXAMPLE 19

Slow Release of Substances

Large microcapsules were prepared by means of an atomization technique. Capsules were of an average size of 350 μm and capsule chemistry was similar to that of Example 4. To measure a release rate, capsules were equilibrated with a tracer solution overnight. A capsule pellet (0.5 ml) was then placed in 5 ml test buffer (PBS) on a shaker and successive aliquots were taken and analyzed. The tracer quantity was assayed using the methods described below. Insulin (Sigma) and OVA were used as tracers. Insulin was assayed by a RIA method by means of Coat-A-Count Insulin Detection Kit (diagnostic Products Corp., Los Angeles, Calif.) and OVA by a protein assay (Bradford) method (Bio-Rad, Hercules, Calif.). The permeability was assessed via an efflux method [11]. Results are listed in Table V. As shown in Table V, permeability can be controlled by means of cation concentration (PMCG, calcium chloride) and by reaction time.

TABLE V

Permeability data for insulin and OVA

| System | | Cation blend | | Reaction time (min) | Zeroeth order rate constant (1/min) | |
|---|---|---|---|---|---|---|
| Anion blend | | | | | insulin | OVA |
| SA-HV | 0.6% | PMCG | 1% | 1.0 | 0.29 | 0.18 |
| CS | 0.6% | $CaCl_2$ | 1% | | | |
| SA-HV | 0.6% | PMCG | 2% | 0.5 | 0.07 | 0.01 |
| CS | 0.6% | $CaCl_2$ | 1% | | | |
| SA-HV | 0.6% | PMCG | 1% | 1.5 | 0.32 | 0.25 |
| CS | 0.6% | | | | | |

EXAMPLE 20

Use of Mucoadhesive Polymers

For antigen delivery to mucosal areas, it is desirable that the outer particulate surface has mucoadhesive properties.

Many polymers listed for multicomponent systems (TABLE I) are believed to be mucoadhesive (heparin, ChS-4, ChS-6, carrageenans, xanthan, gellan, pectin, gelatin, CS, CMC, chitosan). In addition, other polymers can be considered (crosslinked PAA, polymethacrylic acid, hyaluronic acid and collagen). Many uncharged polymers can be incorporated (as an additional component) into the multicationic component (corona) system: HPC, HEC, scleroglucan (SG), polyhydroxymethacrylate (pHEMA), PVP, PVA, PEO, PEG and copolymers of the above. The listed polymers can be used as mucoadhesive polymers as well as polymers exhibiting steric surface stabilization effect (Example 8). Some special substances can also be added to the list: mussel adhesive protein, plant and bacterial lectins and other specialty mucoadhesive polymers. All mucoadhesive polymers can be used in the corona forming mixture in the range of 0.01 to 0.2 wt % in the receiving bath. Thus, the mucoadhesive polymers become integral part of the micro- and nanoparticulate system at processing.

EXAMPLE 21

Nanoparticles for Oral Delivery of Antigen

These particles were generated using a droplet-forming polyanionic solution composed of 0.05 wt-% SA-HV, 0.05 wt-% CS, 0.4 wt-% OVA and 0.012 wt-% PDA in water, and corona-forming polycationic solution composed of 0.05 wt-% SH, 0.065 wt-% PMCG, 0.05 wt-% $CaCl_2$ and 1.0 wt-% F-68 in water. Particles were separated at 15,000 g and incubated in a bicarbonate buffer to carry the crosslinking reaction as described in Example 12. They were again washed and centrifuged at 15,000 g. The average size and charge were evaluated to be 210 nm and 35.1 mV, respectively. The nanoparticles were then introduced orally into the experimental mice (C57B1/6, Harlan, Indianapolis, Ind.). The immunizations were carried at day 0, 7 and 14. At day 21, blood was collected and assayed for the total serum anti-OVA antibodies. Results are summarized in FIG. 5. The immunizations with OVA-nanoparticles resulted in greater levels of serum antibodies than those found with soluble antigen.

EXAMPLE 22

Use of Nanoparticles for Gene Delivery in vivo

These particles were generated using a droplet-forming anionic solution containing 0.025 wt-% pCEPluc plasmid in water, and corona-forming cationic solution composed of 0.05 wt-% Tetronic 904 (BASF) in water. The ratio of droplet- to corona-forming reactants was 1:1. Two reactants were simply mixed together (polyanion added to the polycation) to form nanoparticles. Their size and charge were 190 nm and +24.0 mV, respectively. The particles were resuspended in isotonic 5 wt-% glucose solution and injected intradermally into 5 experimental animals (see Example 9), 0.1 ml per site. Six sites have been applied per animal. Each animal had 2 negative controls (5 wt-% glucose) and two positive controls (5 wt-% glucose, 0.025 wt-% Lipofectamine, 0.025 wt-% pCEPluc plasmid). Animals were harvested after 24 hours by means of 8 mm skin punch. Gene expression was measured by assaying for luciferase activity in minced and permeabilized cell extracts, using a luminometer and data were normalized per protein content. The commercial luciferase assay kit (Sigma) was used. In another set of experiments, empty nanoparticles were used as another negative control with values of RLU/protein close to the negative control.

Figure 5:
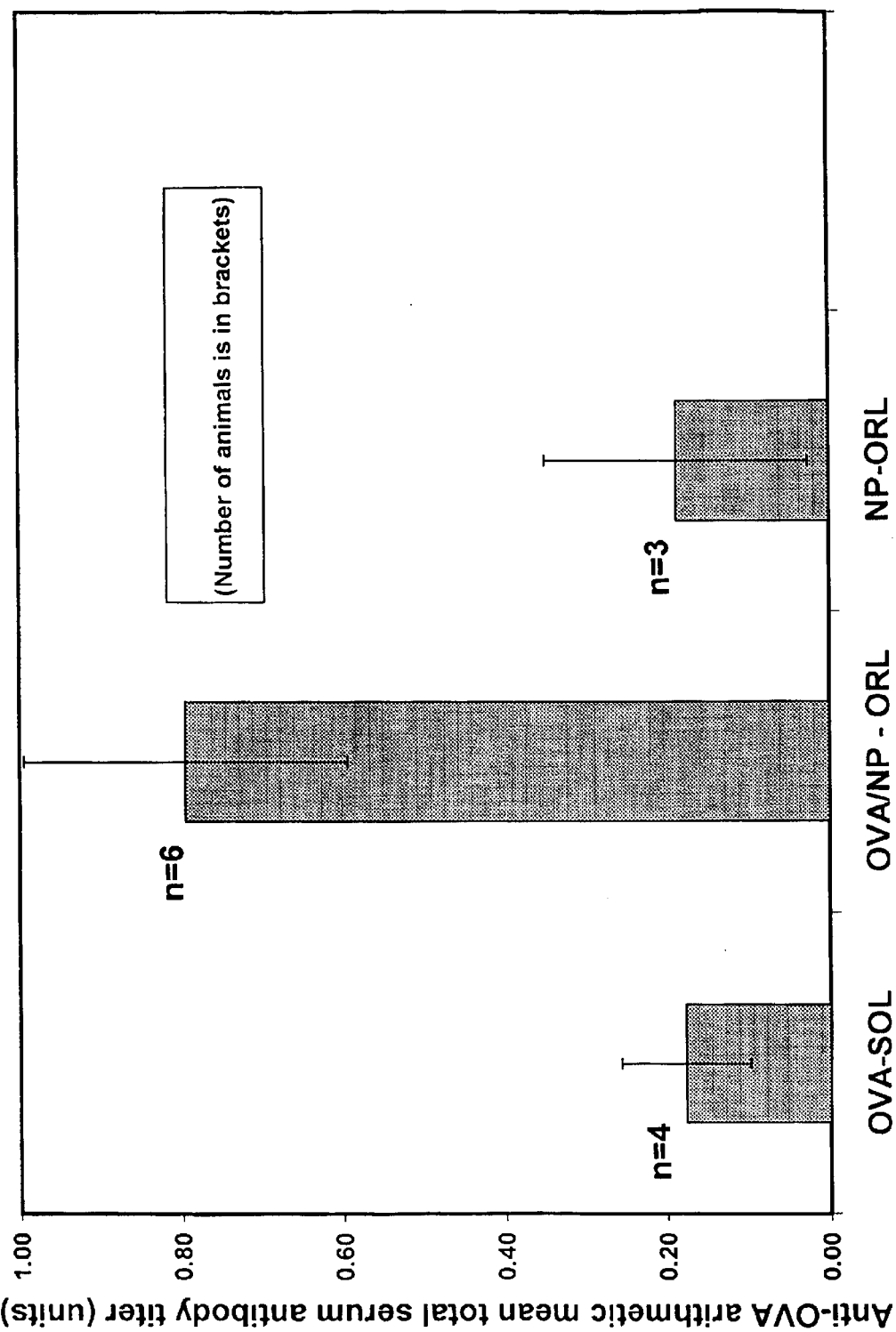
FIG. 5 depicts the response to an oral nanoparticulate OVA antigen (second column) in terms of the total serum anti-OVA antibodies at day 21. The bars represent the average +/−SD. OVA-SOL represents the oral application of soluble antigen; OVA/NP-ORL nanoparticulate formulation and NP-ORL are empty nanoparticles (no OVA).
Figure 6:
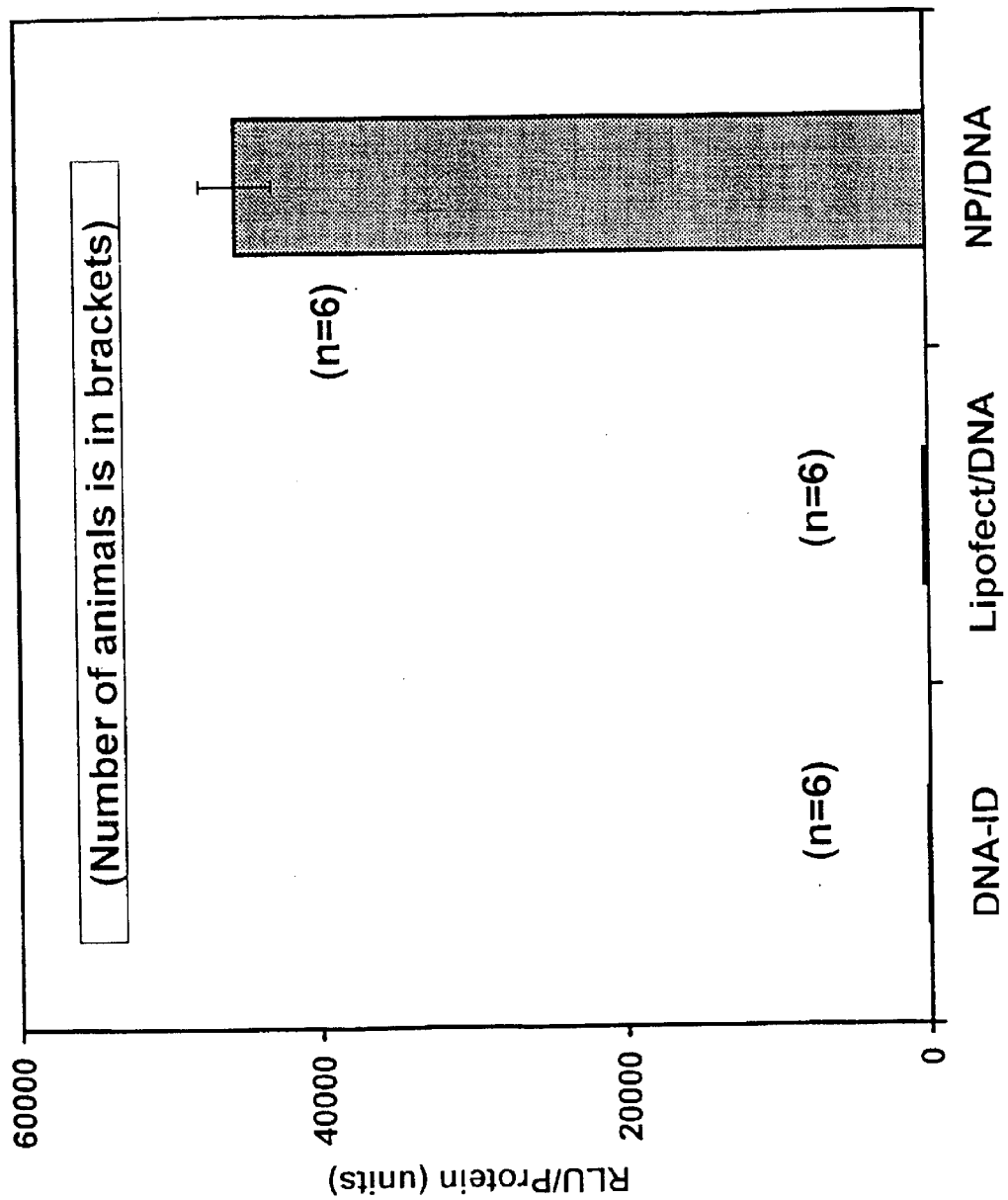
FIG. 6 demonstrates in vivo gene expression. DNA-ID represents intradermal injection of naked DNA solution (plasmid); Lipofect/DNA is DNA complexed with Lipofectamine reagent (Gibco, Gaithersburg, Md.); and NP/DNA is DNA encapsulated in nanoparticles.

Results are presented in FIG. 5. The values presented as a bar height represent the average (n=number of sites) +/−SD. They clearly show that the formulated plasmid can achieve quite efficient gene transfection, many times over the baseline (controls) (about 400 times over the negative control). Similar results were obtained for polyanionic solution containing 0.025 wt-% pCEPluc and 0.005 wt-% SA-HV and polycationic solution containing 0.05 wt-% Tetronic 904 and 0.005 wt-% CaCl2 in water. Some other detergents of the Pluronic and Tetronic series (BASF) worked equally well.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of making nanoparticles comprised of a polyanionic/cationic complex, wherein said nanoparticles do not dissolve in physiological media for at least one day so as to be useful in drug delivery, said method comprising the steps of:

contacting at least two polyanionic polymers with at least two cations, wherein said contacting is by a process selected from the group consisting of capturing a mist of droplets comprising said polyanionic polymers in a liquid comprising said cations; and, capturing a mist of droplets comprising said cations in a liquid comprising said polyanionic polymers.

2. The method of claim 1, wherein said polyanionic polymers are in a solution and said cations are in a solution.

3. The method of claim 1, wherein said polyanionic polymers are provided in a solution, wherein said solution is dispersed as a cloud of droplets.

4. The method of claim 1, wherein said method produces nanoparticles that have a polyanionic core and polyanionic/cationic complex shell (corona) with an excess positive charge on the particle periphery.

5. The method of claim 1, wherein said cations are dispersed as a cloud of droplets and are collected in a polyanionic solution.

6. The method of claim 5, wherein said method produces nanoparticles that have a cationic core and a cationic/polyanionic complex shell (corona) with the excess of negative charge on the particle periphery.

7. The method of claim 1, wherein said polyanions and polycations are mixed together in the ratio of from about 1:1 to about 1:4.

8. The method of claim 4, wherein individual components of the polyanionic polymers and cations are provided in solution at concentrations of 0.01 wt-% to 0.2 wt-%.

9. The method of claim 2, wherein individual components of a cation solution are present at concentrations of 0.01 wt-% to 0.2 wt-%.

10. The method of claim 1, wherein said polyanionic polymers further comprise an anionic antigen or protein, resulting in said antigen or protein being incorporated into the polyanionic/cationic complex formed upon contact of said polyanionic polymers with said cations.

11. The method of claim 1, wherein a nonionic polymeric surface modifier is included in one or more components selected from the group consisting of said polyanionic polymers and said cations, so that said nonionic polymeric surface modifier is incorporated into said polyanionic/cationic complex as a steric stabilizer.

12. The method of claim 1, wherein said cations further comprise a cationic antigen or protein, resulting in said antigen or protein being incorporated into the polyanionic/cationic complex formed upon contact of said cations with said polyanionic polymers.

* * * * *